United States Patent

Knopp et al.

Patent Number: 5,870,167
Date of Patent: Feb. 9, 1999

[54] APPARATUS AND METHOD FOR IMAGING ANTERIOR STRUCTURES OF THE EYE

[76] Inventors: Carl F. Knopp, 2428 Armstrong, Livermore, Calif. 94550; David C. Knopp, 2015 28th Ave. South, Minneapolis, Minn. 55406

[21] Appl. No.: 404,253

[22] Filed: Mar. 15, 1995

Related U.S. Application Data

[63] Continuation-in-part of Ser. No. 91,670, Jul. 14, 1993, Pat. No. 5,474,548.

[51] Int. Cl.$^6$ .................................................. A61B 3/10
[52] U.S. Cl. ........................... 351/212; 351/208; 351/221
[58] Field of Search .................................. 351/205, 208, 351/209, 210, 211, 212, 214, 221, 243, 247; 359/31, 23

[56] References Cited

U.S. PATENT DOCUMENTS

| | | | |
|---|---|---|---|
| 3,762,803 | 10/1973 | Papritz | 351/206 |
| 3,944,342 | 3/1976 | Martinez | 351/205 |
| 3,944,343 | 3/1976 | Mueller, Jr. | 351/214 |
| 4,171,877 | 10/1979 | Karasawa et al. | 351/205 |
| 4,176,937 | 12/1979 | Kawase | 351/206 |
| 4,411,502 | 10/1983 | Lang et al. | 351/206 |
| 4,449,787 | 5/1984 | Burbo et al. | 359/399 |
| 4,504,129 | 3/1985 | Van Iderstine | 351/206 |
| 4,523,821 | 6/1985 | Lang et al. | 351/214 |
| 4,863,260 | 9/1989 | Gersten et al. | 351/212 |
| 5,110,200 | 5/1992 | Snook | 351/212 |
| 5,139,022 | 8/1992 | Lempert | 351/206 X |
| 5,255,211 | 10/1993 | Redmond | 364/578 |
| 5,293,532 | 3/1994 | Marshall | 351/225 |
| 5,347,333 | 9/1994 | Isogai et al. | 351/214 |
| 5,359,372 | 10/1994 | Kida et al. | 351/219 |
| 5,474,548 | 12/1995 | Knopp et al. | 351/237 |
| 5,512,965 | 4/1996 | Snook | 351/212 |

FOREIGN PATENT DOCUMENTS

| | | | |
|---|---|---|---|
| 1-285242 | 11/1989 | Japan | 351/212 |

OTHER PUBLICATIONS

Otto Hockwin, Kazuyuki and Disney Lerman "Evaluating Cataract Development with the Scheimpflug Camera", Chapter 16, 6 pgs.

Primary Examiner—Huy Mai
Attorney, Agent, or Firm—Paul & Paul

[57] ABSTRACT

An apparatus and method provides images of the anterior structure of the eye which can be captured. Various slit lamp projections are captured by a camera utilizing a CCD along the line of sight axis so that all images which are taken are referenced to the line of sight and are reproducible along that axis.

41 Claims, 8 Drawing Sheets

APPARATUS AND METHOD FOR IMAGING ANTERIOR STRUCTURES OF THE EYE

RELATED APPLICATIONS

This application is a continuation-in-part of U.S. patent application Ser. No. 08/091,670 filed Jul. 14, 1993 entitled "Method Of Establishing A Unique Machine Independent Reference Frame For The Eye", now U.S. Pat. No. 5,474,548.

FIELD OF INVENTION

This invention relates to a device for mapping the structures of the eye.

DESCRIPTION OF PRIOR ART

Topographic mapping of the cornea, generally known as keratometry or keratography, has been utilized to both measure the front shape of the cornea and detect corneal shape irregularities. In recent years sophisticated keratography methods have been developed, coupled with computer assisted analysis and display of derived corneal shapes. These methods, combined with an image grabber such as a video camera plus storage device are usually known as videokeratography.

The most common videokeratography method used presently is based on placido disk illumination. Concentric rings of known size and configuration are projected onto the cornea and the sizes and distances of the reflections are measured. Using various algorithms, these measurements are compared to the known sizes and distances, and an image of the anterior surface of the cornea constructed. Examples of placido-based systems are the Topographic Modeling System (TMS) made by Computed Anatomy (Tomey), the EyeSys Corneal Analysis System and the Visio EH-270 Computerized Corneal Topographer from Visioptic, Inc. Examples of the image processing methods and the sophisticated algorithms required in such placido disc based devices have been described by Gersten et al in U.S. Pat. No. 4,863,260 and by Snook in U.S. Pat. No. 5,110,200.

Such methods rely on specular reflection of the concentric rings from the highly reflective tear film of the cornea. Yet these reflections in two dimensions are being used to construct the three dimensional image. This is an important limitation of the placido disk based prior art. The two dimension data used is insufficient to construct a complete three dimensional map. Pits, valleys, or other irregularities may not be adequately conveyed by the reflections in two dimensions and thus an accurate three dimensional image may not be constructed. Furthermore, the algorithms used in the conversion may attempt to compensate for known gaps by using dithering and other extrapolation techniques to "fill-in" the gaps. These extrapolation techniques might make, unknown to the operator, certain assumptions about the surface. This results in the operator being unable to correct for those assumptions, even if he or she wished to. The algorithms might, as well, erroneously assume a constant curvature of the cornea. This is not the case for most individuals.

The technique also often excludes measurement of various parts of the cornea, due to insurmountable mechanical limitations. For example, reflection of the center of the disks provides no information to the system. Thus an area of up to 1 mm or larger might be excluded from the mapping. For another example, the outer one third of the cornea might not be mapped, because the incident pattern makes an increasingly acute angle with the cornea, so that the spatial resolution of the reflected pattern becomes increasingly poor.

There also might be portions of the corneal surface that are simple obscured, due to some anatomical feature, and thus cannot be mapped by the placido disk method at all. Finally, sheer operator error might contribute to erroneous readings.

Taken together, these limitations can result in dioptic errors of 1 to 2 diopters with the errors becoming larger towards the periphery. Key sources of errors common to these techniques are described by Roberts in *Investigative Ophthalmology and Visual Science*, Volume 35, 1994, pages 3525–3532, and *Refractive & Corneal Surgery*, Volume 9, pages 347–357.

There are other technologies currently under investigation which claim to overcome some or all of the above shortcomings. These include raster photogrammetry, specifically the PAR Corneal Topography System (from PAR Technology), laser holography (e.g., the CLAS Corneal Topography Unit from Kerametrics, Inc.) and projected fringe contouring (e.g., in the device made by Visionary Systems, Inc.). However, all of these techniques rely again on specular reflection which must in some cases be enhanced using physical means such as talcum powder. Thus, they again might face the two to three dimensional manipulation problem. So, while enhanced accuracy of the reconstructed surface and coverage of the central zone may be claimed with some of these alternate techniques, they also still have the drawback of decreasing spatial resolution with increasing distance from the center of the cornea.

Perhaps the greatest problem with placido disk or any other reflection technique is the lack of a constant, easily reproducible and verifiable reference point on the cornea. The cornea lacks a structure that can be used as a measurement reference point. Thus any sort of attempt to center the measurements on the cornea or precisely reproduce the map is difficult in a normal diagnostic setting such as a practitioner's office.

This difficulty becomes especially apparent when the attempt is made to correlate reflective techniques, which usually map the corneal surface with other techniques commonly used to measure other aspects of the anterior structure. For example, equipment presently used for measuring corneal thickness consists, typically, of a pachymeter using ultrasonic-ranging for determining the thickness of the cornea at discrete locations on the surface. The pachymetry measurements may be performed manually on an individual point-by-point basis, using commercially available instruments. These generally employ a hand-held transducer probe flexibly connected to a power supply and display means. Examples of such equipment are the Myopach ultrasonic pachymeter available from Myocure, Inc. or the Villasensor, from Cilco, Inc. In using such equipment, a fixation target enables the unexamined eye of the patient to maintain some central-axis stability when the probe is placed on the corneal surface. Difficulties arise with this technique because the measured thickness data must still somehow be correlated with the location at which it is taken even though varying methods for patient alignment are used. As a result, associating corneal thickness data with corneal radius of curvature involves attempting to match two entirely different data sets and often, at best, results in only an approximate correlation of the two. Compounding the potential for inaccuracy in attempting such associations is the use by current topography devices of differing methods to define alignment, methods which cannot necessarily be correlated with pachymetry, or even with each other, without ambiguity.

One other technique that has been utilized is the use of a slit lamp, which illuminates the eye. Measurements are made from the scattered light. Unlike the reflection technique used in placido disk or the ultrasonic ranging of pachymetry, slit lamp scanning involves the acquisition of both anterior and posterior surface profiles in cross section. These profiles are of the entire area because the recorded light originates from particulates in the enclosed region in its entirety.

This is a potentially more desirable method than the others because there is no extrapolation necessary. The profiles are true images of the surfaces. Moreover, thicknesses can also be obtained simultaneously, without the inaccurate or erroneous matching between placido illumination and pachymetry.

However, slit lamp scanning, without more, suffers as well from the lack of a specific reference point on the cornea. In attempts to compensate for this, often a camera, which is used to capture the images generated by the scanning, is fixed along the visual axis with the lateral scanning slit lamp located at a certain angle to the camera and thus to the line of sight. Examples of such arrangement are found in U.S. Pat. No. 5,139,022, where a planar laser slit was scanned transversely across the cornea, in the manner which ophthalmologists have customarily done it. Alternatively, a scanning laser slit lamp could be combined with a photokeratoscope as described by D. J. Grossly et al in Cornea, vol. 7, pp. 30–35, 1988.

Such methods have not enjoyed wide success as they were hindered by mechanical complexity and inordinately long times (as much as a minute or so) required to map an entire cornea. It is improbable to expect the patient to maintain a fixed eye position for that period of time. Furthermore, an arrangement whereby the plane of the slit is always at an angle to the viewing plane is likely to result in distorted data since there is a tacit assumption that the slit plane passes through the nominal center of the cornea—an assumption that cannot easily be fulfilled or even verified on a reliable basis. If, as is likely to happen in practice, the illumination plane intersects the cornea along a line off the approximate center of the cornea the data will generally be skewed along the line and thus non-representative of either the curvature or the thickness for that particular cross section. A further disadvantage is the relatively large depth of focus that is required for the imaging system and the similarly large depth of focus required for the illuminating slit.

Alternatively, both a slit and the camera can be scanned across the cornea, allowing the camera to record the cross section illuminated by the slit at any chosen position. A key problem with such an arrangement is that, in addition to the previous objections, it can also be difficult to obtain a clean image from peripheral regions because of interference from specular reflections, especially from the iris. Such reflections are analogous to noise in the system as they impede or make impossible the extraction of undistorted data. To overcome this, the angle between the camera and the illuminator may be made variable, but that would exact a cost in terms of increasing mechanical complexity, as well as longer times for the measurements.

Still another way used in the prior art to overcome depth-of-field and noise problems was through application of the Scheimpflug principle. See for example, Land et al in U.S. Pat. No. 4,523,821 and Karasawa et al in U.S. Pat. No. 4,171,877. The instruments and methods shown by these patents, however, are very complex optically and mechanically, resulting in equipment that is too expensive for practical implementation in a practitioner's office setting, even as a multi-purpose diagnostic instrument. Neither of them provides for measurement of the surfaces and thickness of the cornea or the construction of a three dimensional accurate representation of it.

In addition to corneal measurement, it may be desirable to measure and examine other portions of the eye, and especially the anterior structures, such as the lens. Complicated and expensive instruments such as the Land and Karasawa inventions permit some of this, however, as set forth above their ease of use is less than desirable for practical implementation.

Thus, there is a great need for a method and apparatus that is capable of producing objective measurements of both corneal shape and thickness that are fully correlated with each other as well as with the reference eye, thus giving the three dimensional geometry of the cornea in a way that is free from the shortcomings and drawbacks accompanying the prior art.

Accordingly, it is an object of the present invention to provide a method and instrument capable of inexpensively examining and measuring the anterior structures of the eye.

It is also an object of the present invention to provide a method and instrument capable of simultaneously measuring the surface contour of the cornea as well as the corneal thickness, and referencing those measurements to a known axis of the eye so that they can be later used with reference to that same axis.

SUMMARY OF THE INVENTION

The present invention overcomes the difficulties inherent in the prior art through a novel arrangement whereby a camera and slit lamp are fixed relative to each other in a single plane. In this configuration, the camera axis is always perpendicular to the image of the slit upon the eye, and hence to the illuminated cross section of the cornea. This fixed entity is then rotated about a predetermined reference axis for the eye, which in the preferred embodiment is the axis of the line-of-sight. Therefore the patient's line of sight lies in the plane of the projected light (illumination) and is always coincident with the axis of rotation. This establishes a common axis for all planes of illumination by the slit lamp.

In this manner the raw data for both pachymetry and topography require no explicit or implicit assumptions in their interpretation and are accurately registered to a patient's line of sight. In a preferred embodiment of the invention a narrow slit of electromagnetic radiation, preferably in the far red to near infrared portion of the spectrum, is imaged upon the cornea. This narrow slit or "slice" of illumination has a length such that it reaches across the entire diameter of the cornea and a width that is narrow compared to the positional accuracy with which the data is to be acquired. The illumination passes through the cornea, a small portion of it being reflected from the anterior surface of the cornea, an even smaller portion from the posterior surface of the cornea, and some being scattered from within the interior structure of the cornea The slice of radiation is rotated about the patient's line of sight as is a data acquisition system consisting generally of video camera and lens system which lies at an angle of approximately 45 degrees to line of sight of the patient while data is being acquired. The data acquisition system is oriented so that it is perpendicular to the cross section of the cornea illuminated by the slice of radiation and is focused upon it. As the camera and illumination systems are rotated, the visual axis of the patient always lies within the plane defined by the optical axis along which the slit is projected and the optical axis along which the data acquisition system views the cornea. This is the result of the patient viewing a unique fixation system which consists of dual targets. While the patient maintains the alignment of these targets the coincidence of the optical axis of the instrument and the visual axis of the patient's eye is maintained in a known and repeatable orientation with respect to the data that is acquired.

The data is taken by positioning the data acquisition and slice of illumination at a desired point, capturing and storing the electronic image into computer memory, then moving to the next position, and so on, until examination of the area of interest has been completed, a procedure which normally involves the rotation of the slice of illumination by 180 degrees. Once all of the captured electronic images have been acquired, they can accurately be referenced to one another because each has a common reference point, namely the intersection of the axes of the optical axis along which the patient is looking and the axis along which the data were acquired.

It is possible and even likely that the patient will experience involuntary eye motion during the time necessary to acquire the electronic images, which in the preferred embodiment can be as long as 15 seconds. If the line of sight of the patient were to deviate from the optical axis of the instrument at any time during the measurement, the final reconstruction of the corneal image from the acquired data would be in error due to the lack of a common reference point for all of the images. Generally, small involuntary movements of the eye have not been found to cause significant error in constructing the three dimensional corneal map but a means for eliminating this potential error has been incorporated into the apparatus of the invention to further improve accuracy. The preferred means consists of a second camera, synchronized with the camera of the data acquisition system, which captures an electronic image of the eye from a region directly along the patient's line of sight. This image, when used in conjunction with the image from the data acquisition camera, provides a measurement in three dimensional space of any deviation of the patient's line of sight from the optical axis of the instrument at the moment that the electronic pictures were taken. With this information it is therefor possible to correct the reference point on any electronic image to reference it to the point defined when the first image was acquired.

An illustrative embodiment of the invention will be described in conjunction with the accompanying drawings, in which:

DETAILED DESCRIPTION OF PREFERRED EMBODIMENTS

Figure 1:
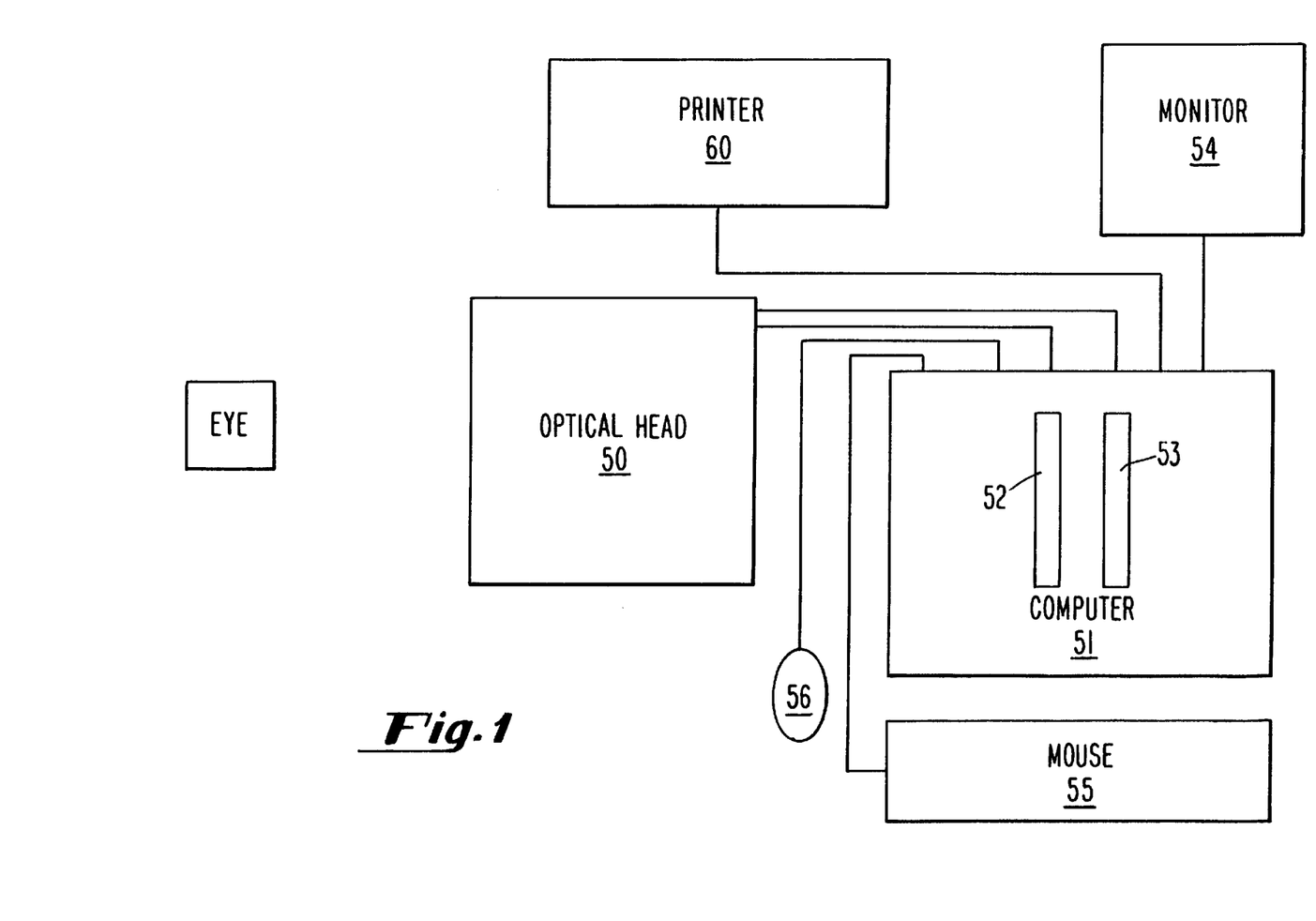
FIG. 1 is a block diagram of the apparatus in accordance with the invention.

FIG. 1 is a generalized block diagram of the apparatus in accordance with the invention. The key elements comprise an optical head 50, containing illumination, image detection and patient interface components and interfaced with computer 51 through control 52 and frame grabber 53. The computer 51, in turn controls the display on monitor 54. Information is supplied to the computer by the operator using either the mouse 55 or the keyboard 56. Optionally, a printer 60 may be controlled by the computer.

Figure 2:
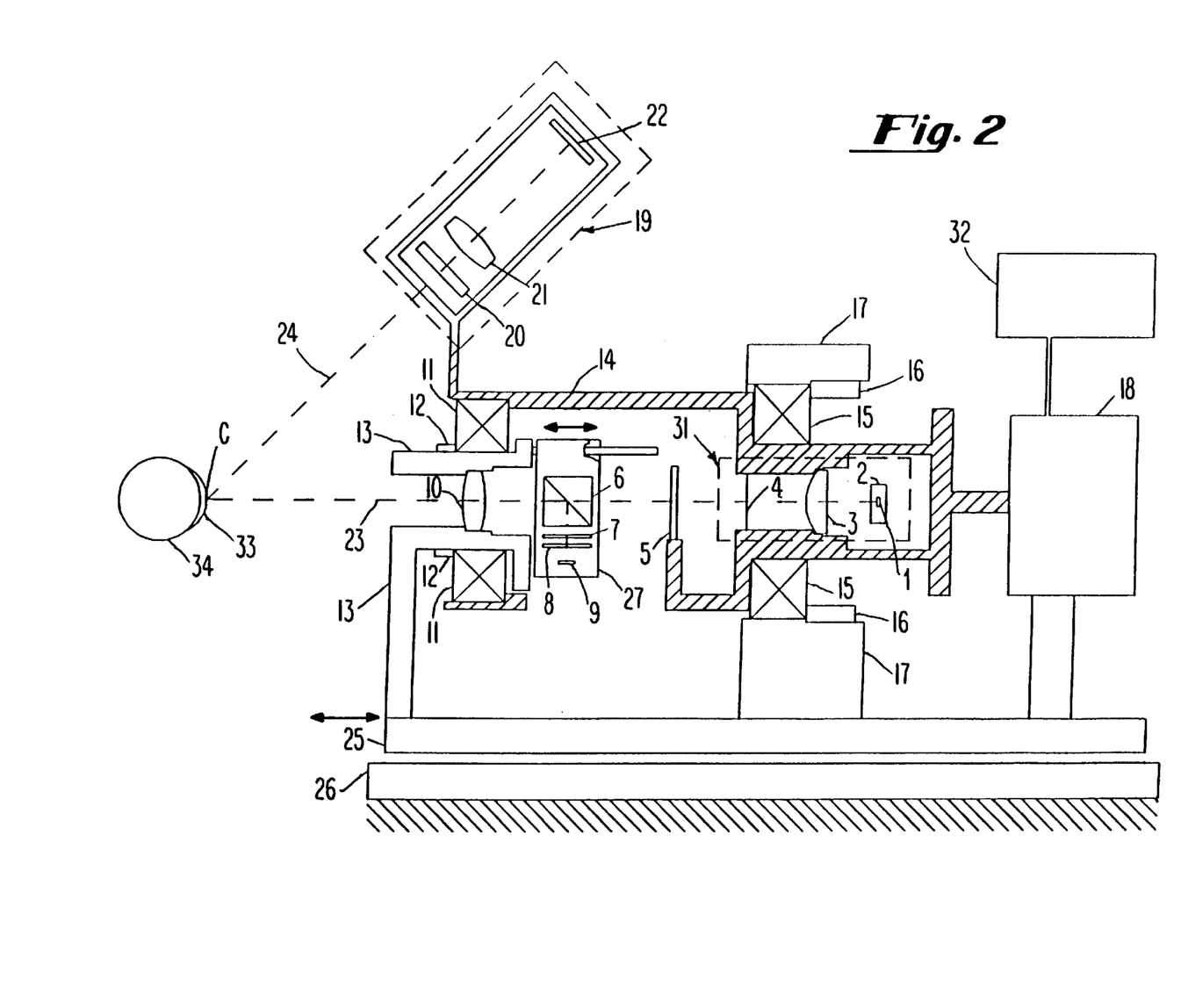
FIG. 2 is a diagram showing construction of the optical and mechanical portion of an instrument of the invention.

FIG. 2 shows schematically the key elements of the approach. Illumination comprising a slit lamp assembly 31 is rotated around the optical axis 23 of the system. Data acquisition is accomplished by simultaneously rotating the image capture assembly 19, which has a viewing axis 24 intersecting the optical axis 23 at a point C on the cornea 33 of eye 34 The camera and slit rotations are mechanically synchronized by means of a rotating member, rotor 14, which is preferably supported on bearings 11 and 15 and to which assemblies 31 and 19 are affixed. It will be appreciated that in a different embodiment the assemblies 31 and 19 could be electronically synchronized and rotor 14 would not then be required.

The slit lamp assembly is comprised of a light source 2, containing a lamp filament 1, from which light is collected and directed upon and through slit 4 by condenser 3, such that a substantially planar light beam is generated. In preferred embodiments a commercially available tungsten light bulb may be used as the light source. However, alternative light sources such as an arc lamp or even a laser beam may be used for differing applications. The light bulb 2 is chosen, preferably, with a rectangular filament. Mechanically, it is affixed to rotor 14 through an electrically insulated mounting so that the filament 1 is parallel to slit 4. Note that in FIG. 1, filament 1 and slit 4 are shown rotated 90 degrees out of the plane of the paper for clarity. In the preferred embodiment of the invention they are both oriented to be perpendicular to the plane defined by the optical axis 23 and the viewing axis 24.

The condenser lens 3 is generally chosen so that the slit is completely illuminated and the lamp filament 1 is imaged into approximately the principal plane of projection lens 10, so as to fill said lens in the direction of the long dimension of the slit. In a preferred embodiment the focal length of the condenser is about 17 millimeters.

Slit 4 is set preferably to about 0.1 millimeters in width and has a dimension along its length of about 13 millimeters, corresponding to the maximum corneal diameter. In FIG. 2, slit 4 is shown affixed to rotor 14 such that its center is collinear with the center of rotation of 14, which in turn is collinear with the optical axis 23. Filter 5 restricts, in the preferred embodiment, the illumination from slit 4 to the red and near infrared portion of the spectrum.

A projection lens 10 projects illumination from slit 4 along the optical axis 23 of the instrument. In the preferred embodiment the image of slit 4 has unity magnification. Located between the projection lens 10 and the slit 4 is a beam splitter 6, the purpose of which is to provide an optical path for the patient to view the alignment assembly 27 while permitting the illumination from slit 4 to pass through lens 10 and be focused at C on the cornea 33. In general the relative aperture of the projection lens 10 is selected such that the depth of focus of the illumination beam is sufficiently long for the beam to remain constant across the thickness of the cornea. In alternative embodiments, in which structures other than the cornea are of interest, the relative aperture of lens 10 should be selected so that the illumination is substantially constant in width across the largest dimension depth extension of the eye. (Relative aperture or f-number is commonly defined as the ratio of focusing lens focal length to lens pupil diameter—see, for example. p. 187 of *Principals of Optics,* 2nd edition, Macmillan Co. of New York, 1964, by M. Born and E. Wolf.)

The alignment assembly 27 as an alignment determining assembly is preferably used to determine a line of sight unique to a given eye, thus allowing it to be registered to the optical axis of instrument for an absolute reference frame. The assembly 27 consists of a beam splitter cube 6, a far field fixation target 7, a near field fixation target 8 and an illumination source 9, which is normally a tungsten incandescent lamp. The use of far and near fixation targets to establish a unique alignment axis for the eye were disclosed in copending U.S. patent application Ser. No. 091,670, entitled "Alignment of Patient for Ophthalmic Surgery", which was filed on Jul. 14, 1993. This copending application did not describe a feature which has been found to be necessary to use the device in practice and which is incorporated into the device disclosed herein. In general, patients being examined by the device disclosed here will not have perfect vision. This means that if the near and far field targets are fixed with respect to the patient, one or both will, in general, be out of focus for the patient, often to the point that one or both of the alignment targets are not sufficiently clear to be used for their intended purpose. In the present device as illustrated in FIG. 2, this shortcoming has been corrected by making the assembly 27 movable with respect to the lens 10 and the eye 34 of the patient, the movement being constrained by a pair of rods 35 to take place only along the optical axis 23. The near and far fixation targets, 8 and 7 respectively, are mounted upon either side of a glass element whose thickness of approximately 3 millimeters is chosen so that they appear to be separated by greater than 10 meters when viewed by a person with normal eyesight. The mounting is performed in a manner guaranteeing that the centers of the targets are aligned when the glass element upon which they are mounted is viewed perpendicularly.

Although it would appear that the fixation targets could be mounted in the path of the light emanating from the slit 4 and collected by lens 10, so that the optical axis 23 passes through their centers, such a mounting will not perform the function of using two points to establish the line of sight as expected. This is due to optical properties introduced into the device by the slit. If the fixation targets are located upon optical axis 23 they will be viewed by the patient against the background of light emanating from the slit. Because one dimension of the slit is very narrow, the slit in that direction acts as a pinhole camera, giving great depth of field, while in the other (long) direction it produces no influence upon the aperture through which the light emanates. When the motion of the eye is parallel to the long direction of the slit the patient will observe the near field fixation target appear to move substantially with respect to the far field when the eye is moved from the optical axis 23, as disclosed in copending U.S. patent application Ser. No. 091,670. However, when the patient's eye is moved perpendicular to the long direction (across the small dimension) of the slit very little or no change in position of the near and far alignment targets will be observed. This is the result of the narrowness of the slit producing a very large depth of field which results in the patient being unable to distinguish a distance between the two targets and thus losing the effect described in copending U.S. patent application Ser. No. 091,670. For this reason, the two fixation targets were removed from the direct viewing path of the patient by means of the beam splitter 6. Additionally, the light from source 9 was filtered by filter 36 to remove any radiation of the wavelength of light passed by filter 5. The illumination of the fixation targets by source 9 was made intense enough to cause the residual red light visible through filter 5 to be rendered substantially invisible to the eye by the intensity of the light passing through filter 36, which light contains substantially none of the wavelengths visible through filter 5.

In a preferred embodiment, the first fixation target is at approximately 0.75 meters optical distance form the eye and the second is further away, preferably at optical infinity, for viewing by an emmetropic person, i.e. one whose vision is normal. In order that targets 7 and 8 be put into focus for persons who are near-sighted, the entire alignment system 27 is moved, so it can be brought closer toward the projection lens 10. Similarly, it may moved away from lens 10 to accommodate persons who are far-sighted. Such adjustments are necessary to allow patients of any vision level to align their own line of sight to the optical axis 23.

The image capture assembly 19 consists of the filter 20, the lens 21 and the camera 22, all of which have the mutual viewing axis 24. The assembly 19 is oriented at about 45 degrees to the optical axis 23 and focused at the point C on the surface of the cornea 33, where 23 and 24 intersect. The image of the slit on cornea 33 at the point C produced by the projection lens 10 makes visible a cross section of the cornea formed by reflection of light from the corneal surfaces and the scatter of light from between these surfaces. This scattered light, which is restricted in the preferred embodiment to the red and infrared portion of the spectrum by filter 5, is imaged upon the camera 22 by lens 21, after passing through filter 20. Filter 20 is preferably a long pass filter which permits only deep red and near infrared light to be transmitted to the detectors within camera 22. Its purpose is two-fold. The first is to reject any visible illumination reflected or scattered from the cornea due to illumination source 9 of the alignment assembly 27. The second purpose is to reject ambient light, particularly that produced by fluorescent lighting. In the preferred embodiment, imaging lens 21 consists of an anamorphic lens assembly designed to produce an image that is more magnified across the cross section, or thickness, of the cornea than along its length, generally having an aspect ratio of about 4. The detectors within camera 22 comprise preferably a CCD array with 512×512 pixel resolution or greater, consistent with maximum sensitivity in the red and near infrared region of the electromagnetic spectrum.

Figure 3:
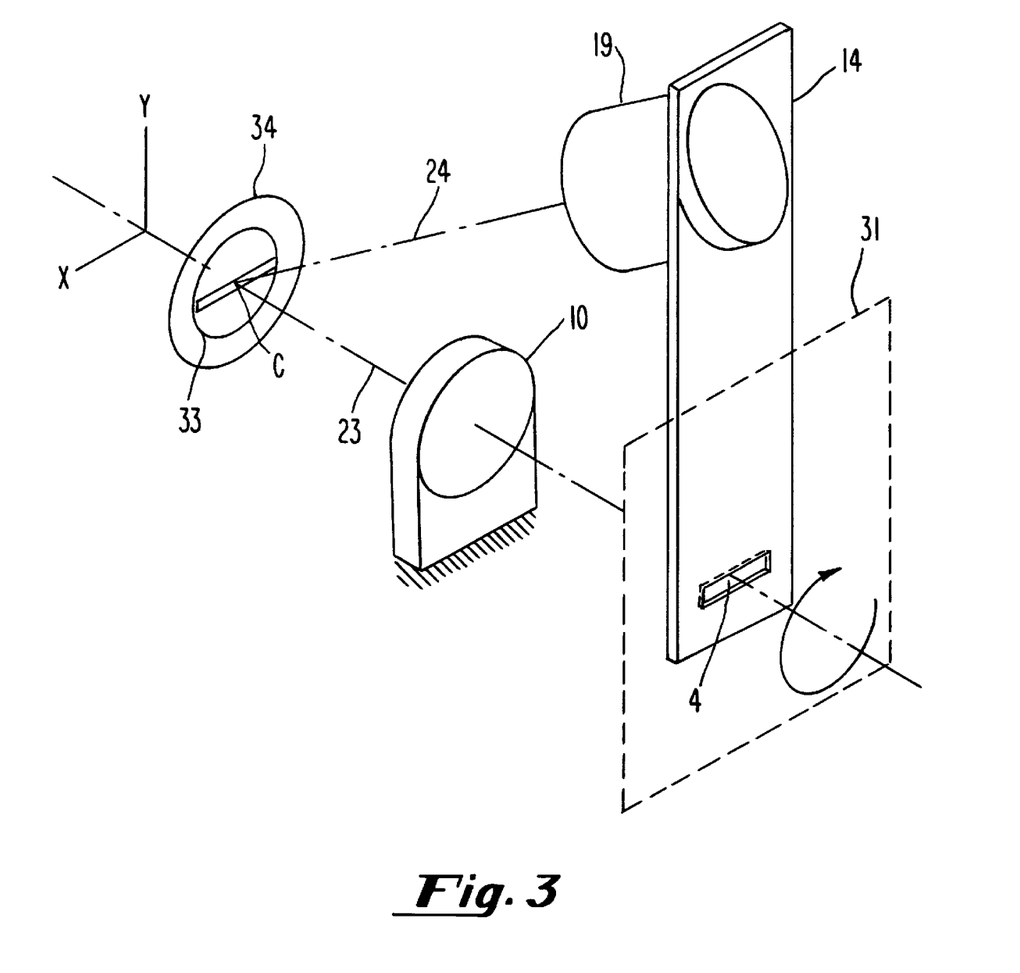
FIG. 3 is shows the geometric relation of the key elements of the apparatus.

In a conventional manner the image detectors convert relative light values into electrical signals, thereby producing a digitized cross sectional image of a given meridian of the ocular tissue under examination, such as the cornea. Using the digitized raw data as input, standard image analysis and processing software can be employed to execute desired operations, including computation of elevations or distances between ocular structures of interest. In a preferred embodiment, algorithms such as described in *Fundamentals of Digital Image Processing*, Prentice Hall of Englewood Cliffs, N.J., 1989, by Anil K. Jain, are utilized to perform edge detection functions leading to profiles of the anterior and posterior corneal surfaces as well as the distance between them, e.g. corneal thickness, at a given location on the eye. Said location, as discussed below, can be made to correspond to a specific meridian The slit lamp assembly 31 and the image capture assembly 19 are both affixed to rotor 14 in the orientation described above. As best illustrated in FIG. 3, this orientation provides the image capture assembly 19 perpendicular to the slit 4 of the slit lamp assembly 31. The rotor is constructed so that it is free to turn on the two bearings 11 and 14 while being driven by motor 18 through a substantial portion of a complete circle, typically exceeding 310 degrees. As shown in FIG. 2, rotor 14 is gripped between the outer race of bearing 15 and the inner race of bearing 11 by means of bearing retainers 16 and 12 respectively. In addition to removing any axial motion of rotor 14 during operation, these bearing retainers are used during construction to move the rotor and all attached pieces along the optical axis 23 so as to position the slit 4 (and all other pieces attached to the rotor) at the proper distance from the projection lens 10. This adjustment is required to accommodate tolerance limits on the focal length of projection lens 10, such limits being the result of requiring a relatively inexpensive lens.

In one preferred embodiment, motor 18 is typically a stepper motor controlled by signals from the motor controller 32 capable of commanding rotor 14 and all attached parts to any desired angular position with respect to an established reference point. Alternatively, motors employing direct current and position sensing, alternating current and a clutch mechanism, or rotation by hand can all be used to accomplish the positioning.

In FIG. 2, the projection lens 10, the beam splitter 6, the filter 5 and the alignment assembly 27 are shown mounted to holder 13 which passes through the inner race of bearing 11 and is mounted to base plate 25. The outer race of bearing 15 is contained within housing 17 which is also attached to base plate 25, as is motor 18. Thus, the slit lamp assembly 31 and image capture assembly 19 can both rotate about the optical axis 23 while all other elements of the invention remain fixed to the base plate 25. Base plate 25 may be moved with respect to the fixed mount 26 to position the entire optical head, consisting of all the elements of FIG. 2, (with the exception of external interfaces such as the eye 34 mount 26 and motor controller 32) closer to or further from the eye. Generally, the base plate 25 is constrained to move only in the direction of the optical axis 23 and is therefore used to establish the proper distance of the instrument from the surface of the cornea 33 such that the image of the slit is in proper focus.

The position of best focus of the slit image is established at the time the instrument is constructed. This is done by positioning a target, which may be either a cylinder or ball with a radius approximating that of the cornea, or a flat plate, at the position of best focus of the image of the slit as projected by the projection lens 10. The position of best focus is ascertained by examining the image of the slit upon the target by means of the image capture system which is operated as a continuous framing camera. The target has a cross hair upon which the image of the illuminated slit is centered. The central pixel of the slit image is found through standard data acquisition methods similar to those used to find the edge of the images of the corneal cross section as was discussed above. The horizontal location of the central pixel is stored in the computer portion of the instrument as a reference pixel, so that it may be used during the operation of the instrument to create a vertical reference line, defining the proper distance of the patient from the instrument.

A similar method is used to establish the absolute calibration of the instrument with regard to spatial distances. This is done through the use of a planar target consisting of a grid with a known dimension between grid elements. The target is placed in a plane parallel to the base 25 with one set of the grid lines appearing horizontal in the camera 22 and such that one of the nodes of the grid is located at point C. The metric for the data acquisition system 19 is then established by measuring the number of pixels in width and height for each unit of the grid. This measurement is made across the entire field of view of the camera 22 and the results, which are referenced to the reference pixel referred to above, are stored in the computer portion of the instrument.

FIG. 3 shows the geometric relationship between the optical axis 23, the image detection axis 24 and the eye 34. The planar view is defined as the view obtained looking along the optical axis 23, and viewing an object in the plane defined by the x and y axes perpendicular to 23. In the operation of the instrument, the patient looks in the direction of, and along, the optical axis 23, moving their head and eye until the origin of the two reticules 7 and 8, appear to be coincident. This establishes the patient's line of sight to be collinear with optical axis 23 of the instrument. Assemblies 31 and 19 rotate around the optical axis 23 passing through the projection lens 10. Illumination of a well defined section of the cornea which is centered on and encompassing the optical axis 23 is thereby achieved at selected angles about the axis 23. Since axis 23 is collinear with the patient's line of sight, a series of cross sections of the cornea is electronically captured, all centered on the same axis and having a common point at the intersection C of the cornea 33 and axes 23 and 24. The coordinates of the edges of these cross sections, referenced to a plane passing through C and parallel to the plane defined by the axes x and y, are subsequently used to construct representations of the front and rear surfaces of the cornea, spaced at the measured distance. Thereafter, the series of surface representations at various meridians may be used to compute one or more three dimensional surface constructions, using conventional numeric techniques. This procedure is generally known as optical tomography and has been given the name Computer Assisted Corneal Tomography (CACT). Details regarding methods for surface construction can be found in *Countouring: a Guide to the Analysis and Display of Spatial Data*, second printing, Pergamon Press of Tarrytown N.Y., 1992, by David F. Watson.

The advantage of the referencing method shown in FIG. 3 is that it allows meaningful comparisons among specific cross sections acquired at a given location but at different times. This could be very useful for determining the progress of certain conditions such as keratoconus. Similarly, the precise referencing of the three dimensional surfaces allows comparisons of refractive changes over time, e.g. before and after refractive surgery.

Figure 4A:
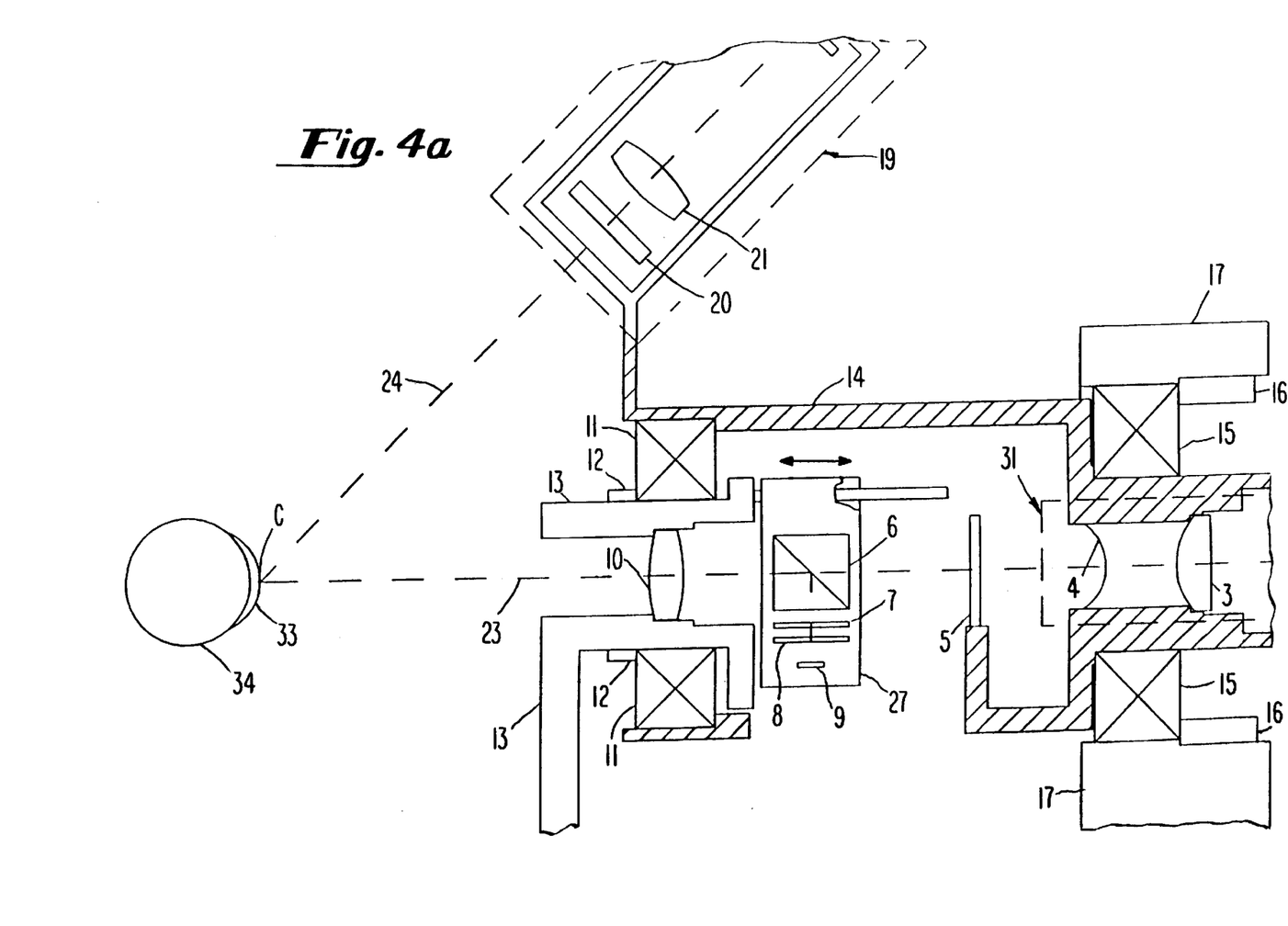
FIGS. 4a and 4b show the manner of use of a curved slit to improve the focus of the projected slit at the cornea.
Figure 4B:
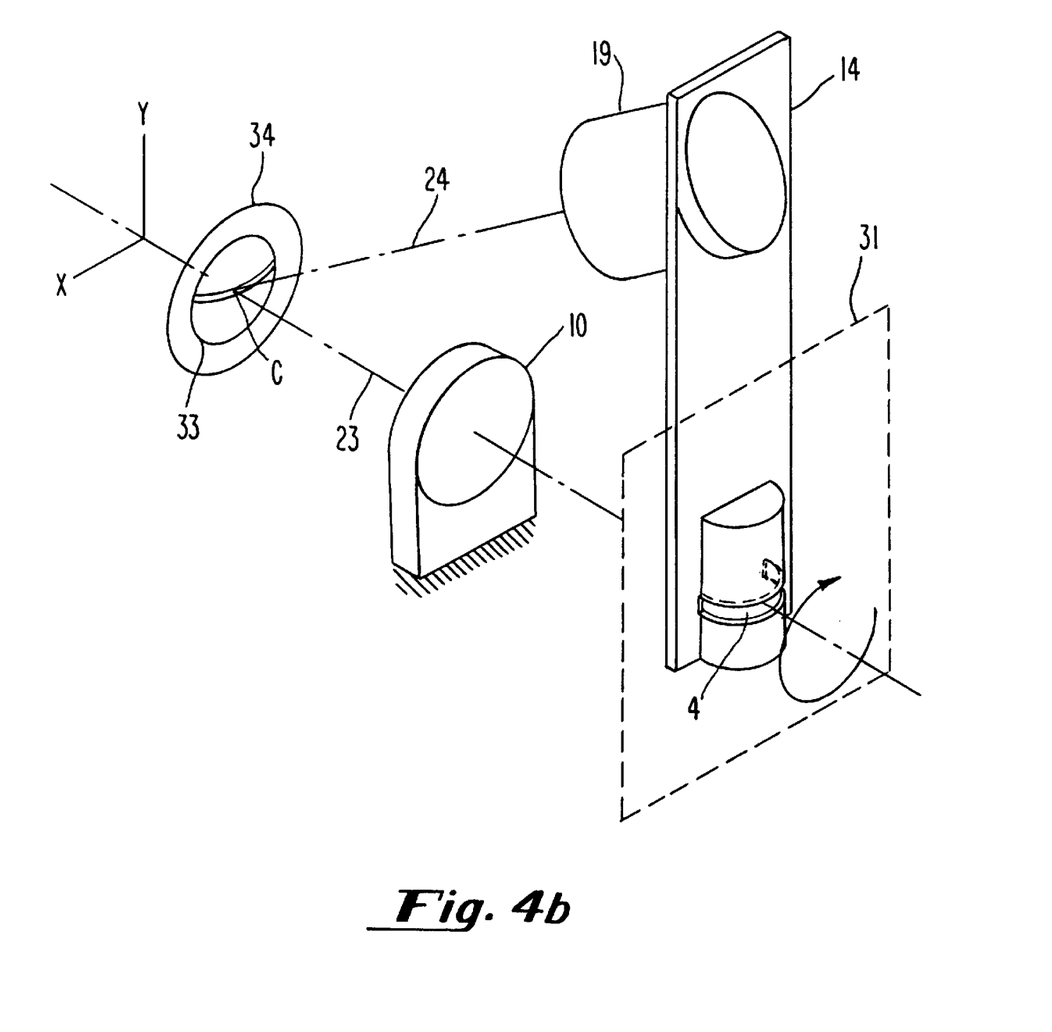

FIGS. 4a and 4b show an embodiment comprising a modified apparatus and a method designed to improve the sharpness of the image of the slit of light comprising the optical probe that is projected onto the cornea. A conventional projection lens will produce, in general, a curved image of a straight object, the curve being concave toward the lens or, if the lens is well corrected, a planar image. Neither of these is desirable in this invention because the slit needs to be as uniform in thickness as possible when passing through the cornea in order that the edges of the front and rear surfaces of the cornea be defined precisely. It is therefore desirable to have the slit of light focus as nearly as possible onto the complete surface of the cornea. This requires that it focus with a shape that is convex toward the projection lens 10, the opposite of the orientation normally encountered in most optical systems. Such shape can be achieved by forming slit 4 as a portion of a cylinder, the long axis of the slit lying upon the circumference of the cylinder. It is oriented concave toward the projection lens 10. Consequently, a focal plane for the slit image is created such that it is curved in the direction opposite to that which would normally be formed with a planar slit, with the result that the image of the slit is brought to focus across substantially the entire surface of the cornea upon which the illumination falls. As in the preferred embodiment, the slit is preferably about 0.1 millimeters in width and measures about 13-mm along its chord corresponding again to a corneal diameter of approximately 13 millimeters.

Figure 5:
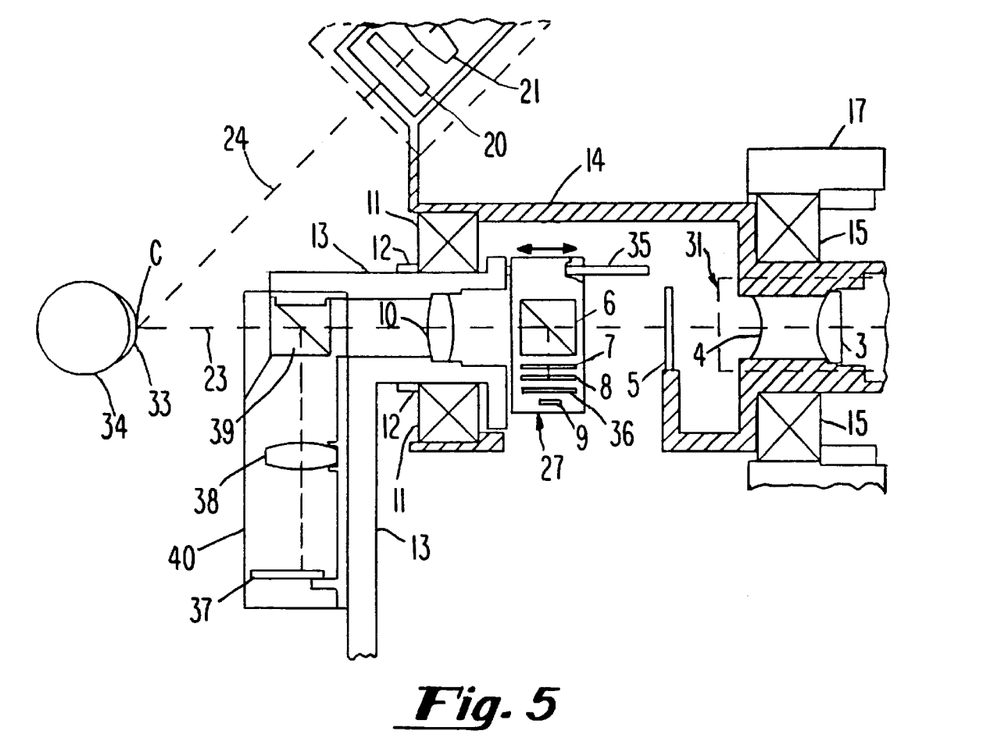
FIG. 5 illustrates the use of a second camera to record the position of eye.

In yet another embodiment, a modified apparatus is shown in FIG. 5 that can compensate for possible movement of the eye during the measurement time. Ideally, if the patient were able to maintain perfect alignment with the fixation points 7 and 8 during the full period of data acquisition then all of the acquired cross sections would have a common point located at the intersection of each cross section, the optical axis 23, and the viewing axis 24. In general, it must, however, be assumed that the patient's eye will undergo some movement during the time of data acquisition, which in the preferred embodiment can be as long as 15 seconds. This means that there is no longer a common point of reference for all of the cross sections obtained during the course of measurement. However, if a method were available for re-establishing the common relationship between all of the cross sections and the intersection of axes 23 and 24, then small amounts of eye motion during the data acquisition period will not interfere with the accuracy of constructing complete corneal surfaces from the acquired cross sections. FIG. 5 depicts a preferred embodiment of an apparatus and method that can provide the information necessary for the combination of cross sections to form an accurate representation of continuous surfaces, even in the presence of small eye motions.

Figure 5A:
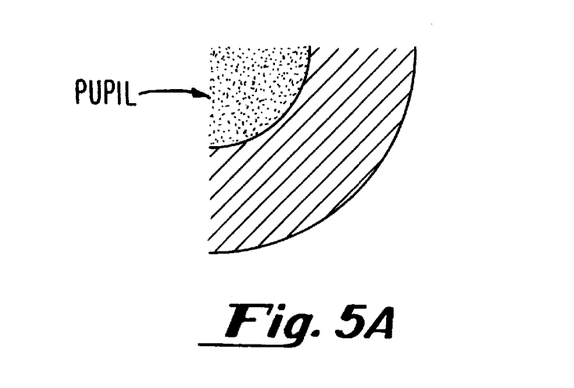

In FIG. 5 is shown an assembly 40 including a beam splitting cube 39 and a lens 38 which are used to form an image of the eye which is centered on the optical axis 23 of the instrument. This image is, in general, larger than the detecting array of the position sensing camera 37. In the preferred embodiment, position sensing camera 37 is located at a distance from the optical axis such that only a portion of the image of the eye falls upon the detecting CCD array, that portion being approximately one quadrant of the generally circular image representing the structure known as the limbus, formed by the juncture of the iris and the sclera (white) of the eye as shown in View A in FIG. 5A. Unlike the pupil of the eye, the limbus does not move or change shape with respect to other portions of the anterior portion of the eye. In general, the sclera and the iris have a difference in light reflecting properties, making the limbus a suitable choice for a visible, fixed structure by which to measure eye movement. The position of a portion of the limbus, or of the entire limbus, with respect to the instrument's optical axis is determined using edge finding techniques similar to those employed to determine the surfaces of the cornea as is discussed above. A measurement is thereby provided of the planar position of the eye with respect to the optical axis 23 of the instrument simultaneously (within the time of one electronic frame) with the image obtained from the image capture assembly. This information is then used in conjunction with the known position of the eye as provided by the obliquely-looking image capture assembly 19 to thereby determine the position of the eye in three dimensional space, relative to the intersection point of the optical axis 23 and viewing axis 24. When such data are collected and stored for each of the cross sectional pictures taken, a subsequent construction algorithm allows the surfaces of the cornea to be accurately calculated from the acquired data.

In alternative embodiments, other methods of eye tracking, such as were disclosed by Knopp et al in U.S. patent application Ser. No. 019,550, "System for Detecting, Measuring and Compensating for Lateral Movement of a Target", may be employed in place of the second camera method of FIG. 5, as long as they are optically coupled to the fixation alignment assembly 27 of FIG. 2. In this regard, the dual target fixation method is of great benefit in so much that it permits data from different instruments to be precisely registered to each other as well as to a specific location on a given eye.

Similarly, any optical diagnostic instrument, such as a specular microscope, may be combined, either on-line or off-line, with the main CACT instrument to provide additional ocular data, all indexed to the same point on the eye. It is therefor the intent of the present patent application to include the possible use of such instruments whether on-line or off-line with the CACT instrument, the features and operation of which are discussed herein.

Figure 6:
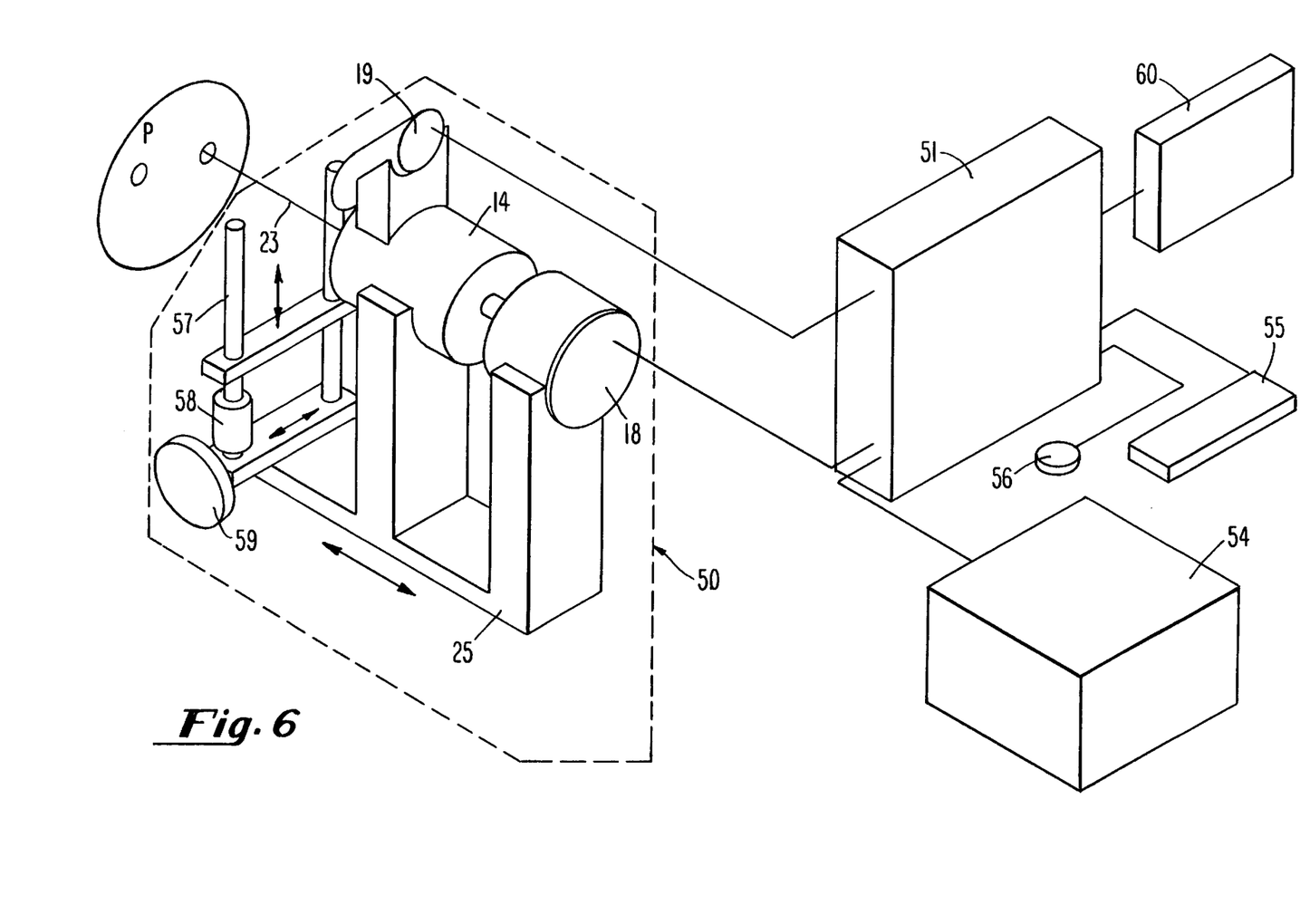
FIG. 6 shows the principal components of entire invention.

FIG. 6 is an isometric drawing showing the principal operational components of the apparatus of the present invention. First the instrument must be positioned at a proper distance from the patient. To do that, a vertical reference line is first displayed by the operator upon monitor 54 using either the mouse 55 or the keyboard 56. This vertical reference line passes through the reference pixel referred to above. Simultaneously, an image of the cross section of the cornea is displayed upon the monitor by the image capture assembly 19, which is operating as a framing camera. The instrument is then moved along its optical axis 23 by moving the base plate 25 as was described earlier. The operator can place the instrument in proper focus upon the cornea by observing the image of the cross section of the cornea and moving the base plate 25 until the vertex of the image of the cross section is tangent to the vertical reference line. The patient head rest 57 includes means for aligning the patient's eye with respect to the apparatus. It is is very similar to the head rests used in many ophthalmic examination instruments, with the exception that lateral movement, in the direction across the patient's eyes, is also provided in addition to the vertical motion usually allowed in these devices. The purpose of this additional motion is to provide the patient with a mechanism to present either eye, such that the eye being examined is always aligned along the optical axis 23 of the optical head 50, unassisted by the operator of the device.

Figure 7:
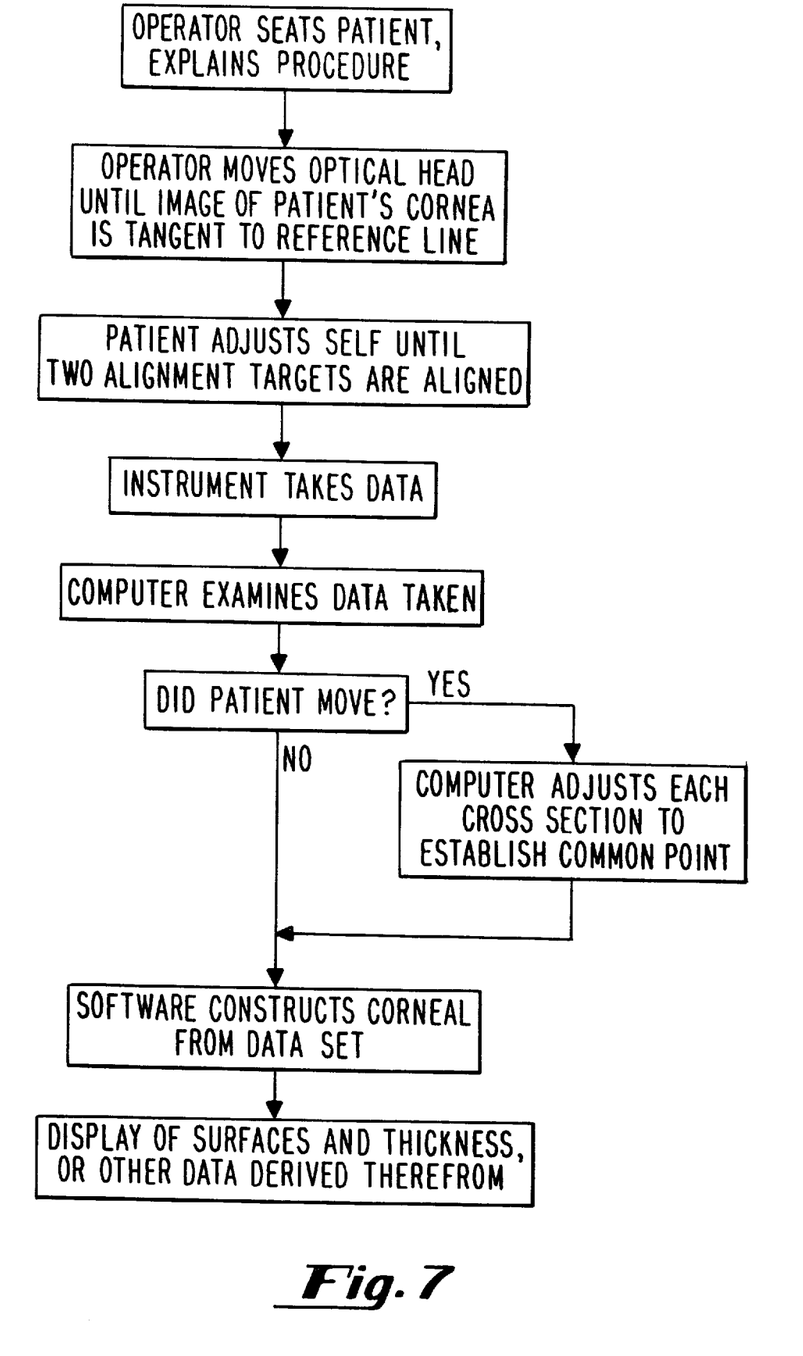
FIG. 7 is a flow chart indicating sequence and operation of the tomography measurement system.

FIG. 7 presents a flow chart of the operation of the invention. In one embodiment, the patient initiates the data gathering process, since it is the patient who perceives when alignment to the optical axis is achieved.

To use the instrument, the patient P places his/hers head into head rest 57 of FIG. 5 while looking toward the optical head 50, which was shown in detail in FIG. 2. The patient moves the head rest by use of the vertical adjustment screw 58 and horizontal adjustment 59 slide until the two registration marks 7 and 8 of the alignment assembly 27 of FIG. 2 appear to be centered upon each other. During this time the operator is adjusting the distance between the optical head 50 and the patient P in the manner described for FIG. 6 above. Once the patient informs the operator that alignment is achieved, the operator verifies the correct position along the optical axis 23 and starts the process of data acquisition by initiating a menu selection from, preferably, a Windows© menu shown on the monitor 54. If this is a routine examination of the complete cornea, the software in the computer 51 will cause the motor 18, part of the optical head 50, to move the rotor 14, also part of the optical head 50. and its attached components to a pre-defined initial position, followed by capture of this image for storage in the memory of computer 51. This establishes the first image of the corneal cross section. The controlling software then causes the motor to move the rotor and its attached components to the next position specified by the software, where it is stopped and the image of the cross section of the cornea at this new angle is again recorded and stored in computer memory. This procedure is repeated until the slit image has been rotated 180 degrees from its initial point, giving complete coverage of the cornea. These stored data are then combined into a three dimensional map of the cornea by use of surface construction algorithms alluded to earlier. This map may be displayed in any one of several different manners upon the monitor 54 using standard computer graphics software. The map can also be stored in the memory of computer 51, or saved as a hard copy by use of color printer 60, optionally attached to computer 51.

The resolution of the corneal map cannot, in general, exceed the number of positions at which the data were acquired. The angular spacing between the positions of data acquisition may however be chosen to be of any magnitude desired. Typically, an angular spacing of 12 degrees is used for a routine examination of the entire cornea. It will be appreciated that a much smaller angular separation over a restricted portion of the cornea has the effect of greatly increasing the resolution of the data acquired and can therefore be employed to form an enhanced the representation of that section of the cornea. This permits, in effect, a "zooming in" function which may be of great use in examining aberrations such as keratoconus in great detail. Because of the nature of the radial scan of the optical probe the tomographic image has the best resolution in the region surrounding the patient's line of sight. The line of sight of the eye extends from the object being viewed to the fovea of the eye, the most sensitive portion of the eye's viewing mechanism. Therefor, the invention provides the highest degree of precision exactly where it is important to have the most accurate measurements.

By providing an accurate construction of the cornea a determination of its optical power can be made on a true point by point basis. The three dimensional representation of the cornea or a portion thereof may be used for aid in preparing for surgery, for contact lens fitting, for historical reference or other ophthalmic usage.

Alternate embodiments of the apparatus and methods of the present invention may utilize a different slit illumination assembly and alternative image processing software to acquire and characterize various properties of ocular structures, including optical density and haze of the lens and/or cornea of the eye, as well as measure thickness of other structures in the eye such as the anterior structure. Specifically, the use of a laser illumination source is compatible with methods of the present invention and may well be advantageous in situations requiring great depth of field, such as measurement of the lens. In particular, the present instrument with its unique data acquisition mechanism is expected to improve upon methods disclosed in U.S. Pat. No. 5,139,022, for the purpose of assessing in vivo properties of ocular tissue such as the lens of the eye.

The above description and the view depicted by the Figures are for purposes of illustration only and are not intended to be, and should not be construed as, limitations on the invention.

Moreover, certain modifications or alternatives may suggest themselves to those skilled in the art upon reading of this specification, all of which are intended to be within the spirit and scope of the present invention as defined in the attached claims.

We claim:

1. An apparatus for imaging anterior structures of the eye comprising:
   means for projecting light onto the eye along a predetermined axis;
   means for capturing an image of said eye aligned at a predetermined angle from said projecting means;
   means for rotating said projecting means and said capturing means about said predetermined axis and
   an alignment determining assembly comprising a first target means and a second target means, each of which is located on a first predetermined axis, with said first target means being closest to the eye, so that visual alignment of said first target means with said second target means results in the eye being aligned along a second predetermined axis.

2. An apparatus as in claim 1, wherein said first predetermined axis is the optical axis of the apparatus.

3. An apparatus as in claim 1, wherein said second predetermined axis is the line of sight axis.

4. An apparatus as in claim 1, wherein said means for projecting light onto the eye along said predetermined axis comprises a slit lamp.

5. An apparatus as in claim 4, wherein the slit lamp comprises means for projecting a convex slit image.

6. An apparatus as in claim 1, wherein the capturing means is a camera.

7. An apparatus as in claim 6 wherein the camera comprises a lens and a means for imaging.

8. An apparatus as in claim 7 wherein said lens comprises a means for focusing.

9. An apparatus as in claim 7 wherein said lens comprises a means for magnifying.

10. An apparatus as in claim 7 wherein said imaging means comprises a CCD array.

11. An apparatus as in claim 1, further comprising processing means for providing said capturing means in at least one pre-defined position and storing said images of said eye captured by said capturing means corresponding to the at least one pre-defined position.

12. An apparatus as in claim 11 wherein said processing means provides said capturing means in a plurality of pre-defined positions and stores said images of said eye captured by said capturing means corresponding to said plurality of pre-defined positions.

13. An apparatus as in claim 12 wherein said plurality of pre-defined positions includes a first and a last position, wherein a position of said projecting means when said capturing means is in said last position is rotated substantially 180 degrees from a position of said projecting means when said capturing is in said first position.

14. An apparatus as in claim 13 wherein said processing means further includes means for providing a three-dimensional representation of said stored images of said eye for analysis.

15. An apparatus as in claim 1 further comprising a second means for capturing an image of the eye, whereby said second capturing means determines a predetermined reference point on the eye.

16. An apparatus as in claim 15 wherein said second capturing means comprises a camera.

17. An apparatus as in claim 1 wherein the means for rotating comprises a motor operatively connected to a rotor.

18. An apparatus as in claim 1, further comprising a head rest for receiving a patient, said head rest including means for aligning the eye of said patient with respect to said apparatus, wherein said aligning means comprises adjustment means for varying a vertical and a horizontal position of the eye with respect to said apparatus.

19. An apparatus as in claim 1, further including means for moving said alignment determining assembly in a direction substantially parallel to said predetermined axis.

20. An apparatus for imaging anterior structures of a patient's eye, comprising:
   a first target means and a second target means, each of which is located on a first predetermined axis, with said first target means being closer to the eye, whereby the patient when viewing the first and second target means with the eye can determine when there is alignment of said first target means with said second target means resulting in the eye being aligned along a second predetermined axis;
   a slit lamp means comprising means for projecting a convex slit image;
   a camera means comprising a lens means and an imaging means, aligned at a predetermined position from said slit lamp means; and
   a motor means operatively connected to a stepper means for rotating said projecting means and said camera means about said second predetermined axis.

21. A method for imaging anterior structures of the eye, comprising:
   providing a means for projecting light and a means for capturing an image;
   aligning the eye along a predetermined axis;
   projecting light onto the eye along said predetermined axis by said projecting means;
   capturing an image of said eye at a predetermined angle from said predetermined axis by said capturing means, with the projecting and capturing occurring during rotation of said projecting means and said capturing means about the predetermined axis.

22. A method according to claim 21, further comprising the step of providing said projecting means and capturing means in at least one pre-defined position and storing data associated with said image of said eye corresponding to the at least one pre-defined position.

23. A method according to claim 22, further comprising the step of providing said projecting means and capturing means in a plurality of pre-defined positions and storing said images of said eye corresponding to said plurality of pre-defined positions.

24. A method according to claim 23, further comprising the step of providing a three-dimensional representation of said stored images of said eye for analysis.

25. A method according to claim 21, where the step of rotating said projecting means and said capturing means about the predetermined axis includes the step of rotating said capturing means and said projecting means by a substantially identical angle about said predetermined axis.

26. A method according to claim 25, wherein said capturing means includes a camera and a lens, said method including the steps of:
   positioning said lens having its longitudinal axis perpendicular to an image detection axis extending between the eye and said lens, and
   positioning said camera perpendicular to said image detection axis.

27. A method according to claim 21 further comprising the steps of:
   capturing a second image of a predetermined reference point on the eye; and
   determining a position of the eye when capturing said second image as compared with said image captured of the eye.

28. A device for imaging anterior structures of the eye, comprising:
   a housing adapted to rotate about a first axis;
   a motor connected to and adapted to rotate said housing;
   a slit lamp mounted within said housing and adapted to rotate therewith about said first axis and further adapted to project a slit image;
   a lens provided at spaced separation from said slit lamp, said lens further adapted to focus said slit image from the slit lamp and transmit said slit image to the eye;
   a first camera mounted on said housing and adapted to rotate therewith, said first camera being adapted to record the slit image projected on the eye;
   an alignment determining assembly for identifying when the eye is aligned along a predetermined axis, said alignment determining assembly including a beam splitter cube located in the housing between the lens and the slit lamp and positioned on the first axis of the housing, said beam splitter cube being adapted to translate a reflected image of a pair of fixation targets mounted in the housing at spaced separation through 90 degrees from the axis of rotation of the housing to the eye; and
   a second camera mounted within the housing and adapted to record a reflected image of the eye.

29. A device according to claim 28 wherein said slit lamp includes a substantially planar slit therein for projecting a substantially planar slit image.

30. A device according to claim 28 wherein said slit lamp includes a substantially convex slit therein for projecting a substantially convex slit image.

31. A device according to claim 28 further including a filter mounted within the housing between the beam splitter cube and the slit lamp.

32. A device according to claim 28 further including a beam splitting cube and a second lens mounted within said housing between the second camera and the eye.

33. A device according to claim 28 wherein the alignment assembly further includes means for adjusting a position thereof along said first axis.

34. A device according to claim 33 wherein the alignment assembly further includes an illumination member for providing a source of light through the pair of fixation targets.

35. A device according to claim 34 wherein the alignment assembly further includes a filter positioned between the illumination member and the pair of fixation targets.

36. A device according to claim 28 further including processing means for providing said first and second cameras in at least one pre-defined position and storing said images recorded by said first and second cameras corresponding to said at least one pre-defined position.

37. A device according to claim 36 wherein said processing means provides said first and second cameras in a plurality of pre-defined positions and stores said images recorded by said first and second cameras corresponding to said plurality of pre-defined positions.

38. A device according to claim 37 wherein said plurality of pre-defined positions includes a first and a last position, wherein a position of said slit image when said first and second cameras are in said last position is rotated substantially 180 degrees from a position of said slit image when said first and second cameras are in said first position.

39. A device according to claim 37 wherein said processing means further includes means for providing a three-dimensional representation of said stored images for analysis.

40. A slit lamp assembly comprising:
a light source; and
a means for projecting convex slit images.

41. An apparatus as in claim 40 wherein said slit lamp assembly further comprises a lens.

* * * * *

UNITED STATES PATENT AND TRADEMARK OFFICE
CERTIFICATE OF CORRECTION

PATENT NO. : 5,870,167
DATED : 2/9/99
INVENTOR(S) : Carl F. Knopp; David C. Knopp It is certified that error appears in the above-identified patent and that said Letters Patent are hereby corrected as shown below:

Col 5, line 61, "figure" should be replaced with --figures--.
Col 5, line 61, after "5" and before "illustrates" please insert --and 5a--.

Signed and Sealed this

Seventeenth Day of August, 1999

Attest:

Q. TODD DICKINSON

*Attesting Officer*   *Acting Commissioner of Patents and Trademarks*